United States Patent
Pan et al.

(10) Patent No.: US 6,635,758 B2
(45) Date of Patent: Oct. 21, 2003

(54) PROCESS FOR EXTRACTING GLYCOSIDE USING AN AQUEOUS TWO-PHASE SYSTEM

(75) Inventors: I-Hong Pan, Hsinchu (TW); Chu-Hsun Lu, Kaohsiung (TW); Hsi-Ho Chiu, Hsinchu (TW); Lain-Tze Lee, Hsinchu (TW); Hsin-Jan Yao, Yunlin (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/042,311

(22) Filed: Jan. 11, 2002

(65) Prior Publication Data

US 2002/0058805 A1 May 16, 2002

Related U.S. Application Data

(63) Continuation-in-part of application No. 09/888,627, filed on Jun. 26, 2001, now abandoned.

(30) Foreign Application Priority Data

Aug. 23, 2001 (TW) .......................................... 89119776 A

(51) Int. Cl.$^7$ .............................. C07H 1/06; C07H 1/08
(52) U.S. Cl. ...................... 536/128; 536/1.11; 536/124; 536/127
(58) Field of Search ................................. 536/1.11, 124, 536/127, 128

(56) References Cited

PUBLICATIONS

Minami et al. J. of Chromatogr. B, 711 (1998) 309–312.*
Truust et al. J. of Chromatogr. B, 680 (1996) 71–80.*
Rito–Palomares et al. J. of Chromatogr. B, 680 (1996) 81–89.*
Hermandez et al. J. of Chromatogr. B, 680 (1996) 171–181.*

* cited by examiner

*Primary Examiner*—James O. Wilson
*Assistant Examiner*—Patrick Lewis
(74) *Attorney, Agent, or Firm*—Rabin & Berdo, P.C.

(57) ABSTRACT

An aqueous two-phase system for extracting glycosides from a herb includes the extractive solution, about 5 wt %–30 wt % of salt, about 5 wt %–30 wt % of polyol and selectively about 0 wt %–30 wt % of alcohols. The salt can be dihydrogen phosphate, hydrogen phosphate and phosphate or a mixture thereof, and it also can be sulfates, chlorides, oxalates, or acetates. In addition, a process for extracting glycosides using an aqueous two-phase system is disclosed. The procedures includes preparation of extractive solution, concentration, phase separation, drying, washing with solvent, cooling, filtration and drying of the final products.

37 Claims, 2 Drawing Sheets

PROCESS FOR EXTRACTING GLYCOSIDE USING AN AQUEOUS TWO-PHASE SYSTEM

This is a continuation-in-part of application Ser. No. 09/888,627, filed Jun. 26, 2001, now abandoned.

This application incorporates by reference Taiwanese application Serial No. 89119776, filed Aug. 23, 2001.

BACKGROUND OF THE INVENTION

1. Field of the Invention

The invention relates in general to a technique of extraction to obtain the product with high concentration and high recovery yield, and more particularly to the extracting glycosides from a herb using an aqueous two-phase system.

2. Description of the Related Art

With the rapid development of biotechnology, the techniques of separating and extracting biologically important compounds from animal and plant sources have become an area of great importance. The problems of traditional separation technologies include low recovering yields, and, especially, low yield resulting from fermentation of the solution due to the long period of extraction. These problems hinder the development of medication to a certain extent. The traditional process of separation and purification depend on the chemical and physical properties of materials and products, however, the method mainly applied is that of chromatography. There are several drawbacks to the use of traditional solvents and chromatography including:

1. The process of extraction is time-consuming.
2. Solvents such as dichloromethane or chloroform applied in the process of extraction are toxic and hazardous to human, as well as cause serious environmental pollution.
3. The cost of the process is high.
4. Undesired chemical reactions occur during purification.

SUMMARY OF THE INVENTION

The objective of this invention, therefore, is to develop a method of phase separation using an aqueous two-phase system to obtain the product with high concentration and high recovery yield, which possess advantages such as simple procedures and equipments, low-cost production, and partial recycling and reuse of materials used in the process.

According to the objective of present invention, a process for the extraction of glycosides from herb described as follows:

(a) A herb is ground and mixed with water and then agitated. After filtration, the first filtrate is collected in a beaker while the residue is removed and mixed with water and filtered again. An aqueous extractive solution is made up of the first and the second crude extracts.

(b) The aqueous extractive solution is concentrated to about 1–10% of solid content.

(c) 5 wt %~30 wt % of salt, 5 wt %~30 wt % of polyol and 0 wt %~30 wt % of alcohol are added to the concentrated solution and mixed thoroughly. Phase separation is then carried out at a temperature between 4° C. to 90° C., after which the aqueous layer is separated from the polyol layer. The preferred temperature is in the range of room temperature to 70° C.

(d) The aqueous layer is removed from the two-phase system, and concentrated in vacuo to give a solid which is dried.

(e) The resulting solids in step (d) is then suspended with a solvent to a concentration of 60%~99%, and then sonicated. The first filtrate and residue are then obtained after centrifugation and filtration.

(f) Repeat step (e) at least once, to obtain the second filtrate and residue.

(g) The first and second filtrates are combined and concentrated in vacuo to give the final solid product rich in glycosides.

According to the objective of present invention, another process for the extraction of glycosides from herb is further provided. Steps (a)~(f) are the same as the process abovementioned. After step (f), the first and second filtrates are combined and sitting on the bench for about 12~18 hours at a temperature between −110° C. to 15° C., which the preferred temperature is in the range of −10° C. to 10° C., and the depositions are removed by means of filtration to obtain a final filtrate. Then, the final filtrate is concentrated in vacuo to give the final solid product rich in glycosides.

The invention achieves the extraction of glycosides from a herb by providing a new aqueous two-phase system separation method that includes an aqueous extractive solution, 5 wt %~30 wt % of salt, 5 wt %~30 wt % of polyol, and selectively 0 wt %~30 wt % of alcohol. The salts can be dihydrogen phosphate, hydrogen phosphate, phosphate, or a mixture thereof; it also can be sulfates, chlorides, oxalates, or acetates.

BRIEF DESCRIPTION OF THE DRAWINGS

Other objects, features, and advantages of the invention will become apparent from the following detailed description of the preferred but non-limiting embodiments. The description is made with reference to the accompanying drawings in which.

DESCRIPTION OF THE PREFERRED EMBODIMENT

First Embodiment

Figure 1:
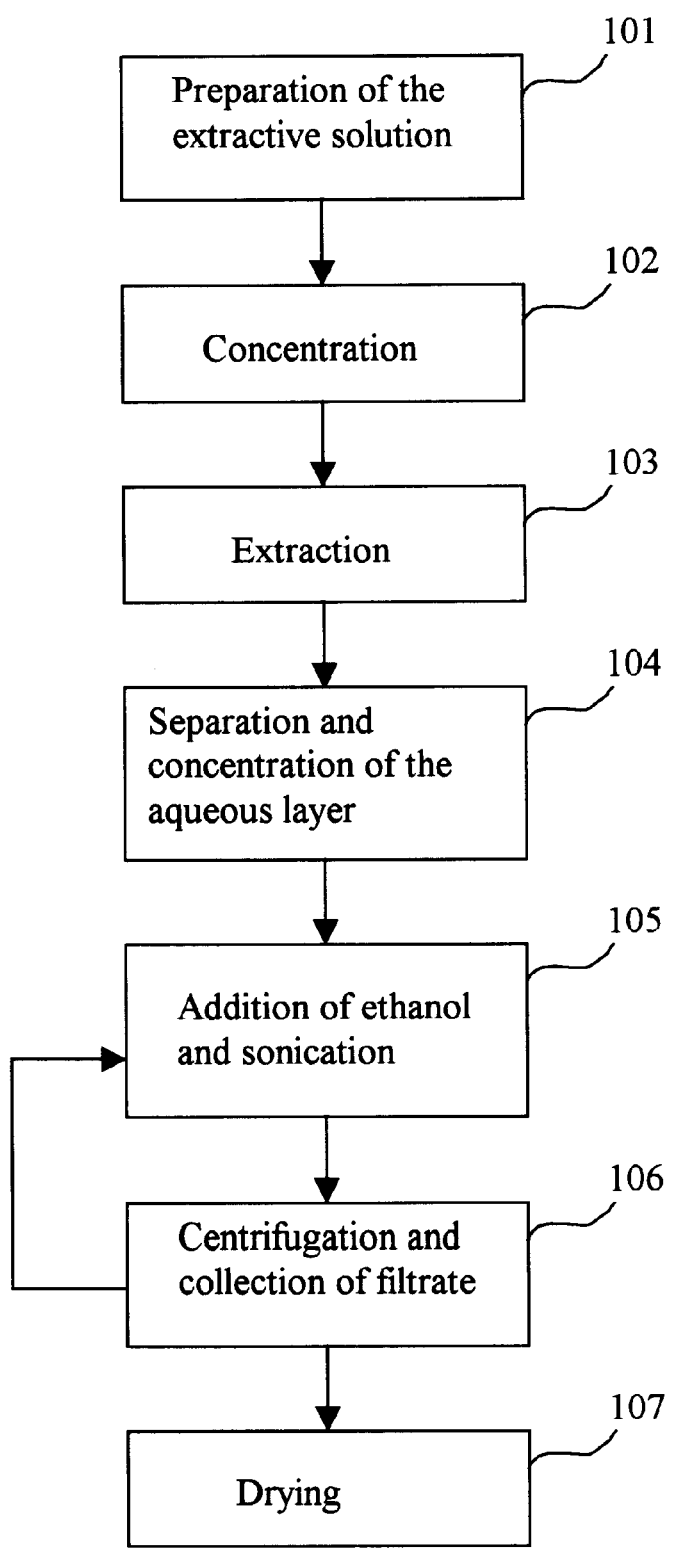
FIG. 1 shows the procedures of extracting glycosides from a plant such as a herb using an aqueous two-phase system according to the first embodiment of the invention.

One process of extraction of glycosides from plants such as herbs using an aqueous two-phase system is presented in FIG. 1. In step 101 (extractive solution), the extractive solution is prepared by addition of crushed herbs or plants to a suitable amount of water such that the herb is covered completely by the water. The extraction can be improved by agitating the mixture. The mixture is filtered and the residue is placed into water again; this step could be repeated several times. Whether the solution is heated or boiled depends on the properties of the material (herbs or plants) such as difficulty of extraction and sensitivity to temperature.

The next step (102) is concentration, as shown in FIG. 1. The extractive solution is preferably concentrated to 1–10% of its solid content. Whether this step is performed depends on the situation of extraction; sometimes it is not necessary to concentrate the extractive solution.

The invention of extraction using an aqueous two-phase system is disclosed in step 103. The aqueous two-phase system is preferably carried out by using an aqueous extraction solution, 5 wt %~30 wt % of salts, and 5 wt %~30 wt % of polyol such as PE62 (Copolymer (20/80) of ethylene oxide and propylene oxide). The salts can be dihydrogen phosphate, hydrogen phosphate, phosphate, or a mixture thereof; it also can be sulfates, chlorides, oxalates, or acetates. The aqueous two-phase system is obtained by the addition of salts and polyol to the concentrated extractive solution (prepared in step 2) or extractive solution (prepared in step 1), and then mixed thoroughly. The phase separation is carried out at a temperature between 4° C. to 90° C., with a preferred temperature range of 25° C. (room temperature) ~70° C. It is more preferable to treat it with a water bath, thereby improving the separation of the water layer and polyol layer. In addition, the aqueous two-phase system is preferably generated by addition of alcohols ($C_1$–$C_4$) such as 0.5 wt %~30 wt % of ethanol.

In step 104, the aqueous layer is removed from the two-phase system, preferably performed by centrifugation and filtration, and concentrated in vacuo to give a solid which is dried.

Then, the solid is washed with a solvent (60%~99%) such as ethanol, as shown in step 105. After sonication, the solution is centrifuged and filtered to separate the filtrate and residue, as shown in step 106, and residue is removed and washed with solvent again. Steps 105 and 106 can be repeated in order to obtain glycosides from the solids adequately.

Finally, all of the filtrate collected from step 106 is preferably concentrated in vacuo to obtain a final solid product rich in glycosides, as shown in step 107.

According to the first embodiment of the invention, monosaccharide, disacchride and polysacchride, such as sennoside, geniposide, paeoniflorin, glycyrrhizin, quercitrin, puerarin, hesperidin, ginsenoside Rb1 and naringin, are extracted efficiently from herbs using the aqueous two-phase system.

The examples 1, 2 and 3 of the first embodiment illustrate the extraction of glycosides from dried gardenia fruit, rhubarb, and the root of herbaceous peony using an aqueous two-phase system.

EXAMPLE 1

Extracting glycosides from dried gardenia fruit using an aqueous two-phase system.

1. 5 g of dried gardenia fruit was mildly ground, mixed with 100 g of water, and boiled for 30 minutes. After filtration, the filtrate was collected and the remaining gardenia fruit was mixed with fresh water, boiled, and filtered. The aqueous extractive solution was obtained by combining the two filtrates.
2. 155.59 g of the extractive solution is concentrated to 21.79 g. The solid content of the extractive solution concentrate is approximately 8.23% and this solid contains 26.93 wt % of geniposide as determined via HPLC.
3. 1.64 g (7.5%) of potassium dihydrogen phosphate ($KH_2PO_4$), 1.09 g (5%) of PE62 and 2 ml (10%) of ethanol are added to the extractive solution concentrate and then mixed thoroughly. The phase separation is performed by keeping the solution in a water bath at a temperature of 70° C. for 1–1.5 hour.
4. After phase separation, the lower layer is the aqueous while the upper layer is PE62. The aqueous layer is carefully removed and concentrated in vacuo to give a solid which is dried.
5. 5–10 ml of 95% ethanol is added to the dried solid, and the mixture is sonicated for 3 minutes.
6. Subsequently, the mixtures are centrifuged and the solid remaining is collected in a beaker. 5–10 ml of 95% ethanol was added to the residue (solids), followed by sonicating for 3 minutes.
7. Thereafter, the filtrate was separated from the residue by centrifugation Concentration of the filtrate in vacuo gave a solid which is dried. The weight of solid product was 0.79 g and the geniposide was 318.44 mg determined by means of HPLC. The ratio of geniposide was 40.31%.

In this case, the purity of geniposide is increased from 26.93% to 40.31% using the aqueous two-phases system. This process improves the purity of the glycosides.

EXAMPLE 2

Extracting glycosides from rhubarb using an aqueous two-phase system.

1. 10 g of rhubarb was mildly ground and mixed with 300 g of water. The mixture was agitated (200 rpm) at room temperature for 30 minutes. After filtration, the filtrate was collected as the aqueous extractive solution.
2. 115 ml of the extractive solution is concentrated to 20 ml. The solid content of the extractive solution concentrate is approximately 6.43% and this solid contains 3.71 wt % of sennosides as determined via HPLC.
3. 1 g (5%) of sodium biphosphate ($Na_2HPO_4$), 2 g (10%) of PE62 and 4 ml (20%) of ethanol are added to the extractive solution concentrate and then mixed thoroughly. The phase separation is performed by keeping the solution in a water bath at a temperature of 70° C. for 1–1.5 hour.
4. The lower layer (aqueous) is separated from the upper layer (PE62) using centrifugation (3000 rpm). Then, the water layer is carefully removed and concentrated in vacuo to a dry solid.
5. 5–10 ml of 70% ethanol is added to the dried solid, and the solution was sonicated for 3 minutes.
6. Subsequently, the phases are separated by centrifugating and the filtrate is collected in a beaker. 5–10 ml of 75% ethanol is added to the residue (solids), and the mixture is sonicated for 3 minutes.
7. Thereafter, the filtrate is separated from the residue by centrifugation. The combined filtrate is concentrated in vacuo to dryness. The weight of solid product is 0.40 g and the sennosides is 24.2 mg as determined by HPLC. The ratio of sennosides is 6.05%.

In this case, the purity of sennosides is increased from 3.71% to 6.05% using aqueous two-phases system. This process improves the purity of the glycosides.

EXAMPLE 3

Extracting glycosides from the root of herbaceous peony using an aqueous two-phase system.

1. 10 g of root of herbaceous peony was mildly ground, mixed with 200 g of water, and boiled for 60 minutes. After filtration, the filtrate was collected and the remaining root of the herbaceous peony was again mixed with water, boiled, and filtered. The aqueous extractive solution was obtained by combining the filtrates.
2. 158 g of the extractive solution is concentrated to 40.65 g. The solid content of the extractive solution concentrate is approximately 4.52% and this solid contains 1.36 wt % of paeoniflorin as determined via HPLC.
3. 3.2 g (8%) of sodium dihydrogen phosphate ($NaH_2PO_4$), 4.8 g (12%) of PE62 and 4 ml (10%) of ethanol are added to the extractive solution concentrate and then mixed thoroughly. The phase separation is performed by keeping the solution in a water bath at a temperature of 70° C. for 1–1.5 hour.

4. The lower layer (aqueous) was carefully removed from the upper layer (PE62) and concentrated in vacuo to a dry solid.
5. 5–20 ml of 95% ethanol is added to the dried solid, and the solution was sonicated for 30 minutes.
6. Subsequently, the phases are separated by centrifugation and the filtrate is collected in a beaker. 5–20 ml of 95% ethanol was added to the residue followed by sonicating for 30 minutes. The mixture was kept at room temperature overnight.
7. Thereafter, the filtrate was separated from the residue by centrifugation. The combined filtrates were concentrated in vacuo to dryness. The weight of solid product was 0.69 g and the paeoniflorin was 13.8 mg as determined by HPLC. The ratio of paeoniflorin was 2%.

In this case, the purity of the paeoniflorin is increased from 1.36% to 2% using aqueous two-phases system. This process improves the purity of the glycosides.

Second Embodiment

Figure 2:
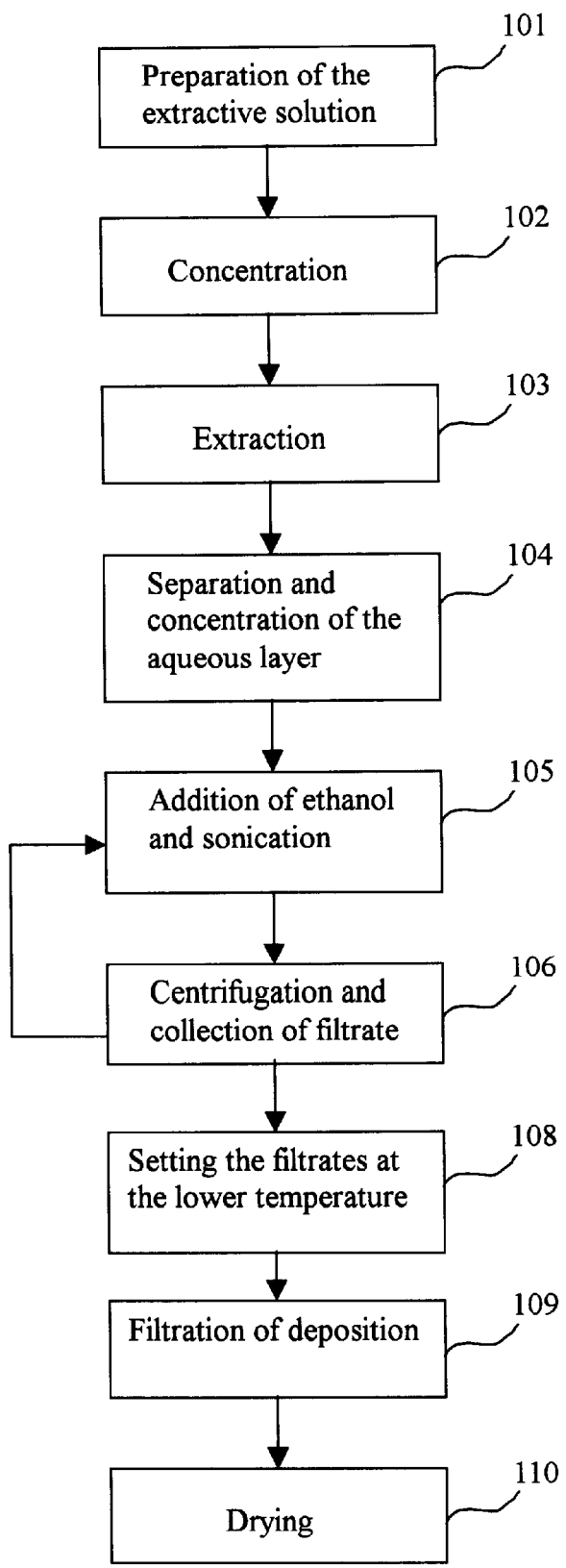
FIG. 2 shows the procedures of extracting glycosides from a plant such as a herb using an aqueous two-phase system according to the second embodiment of the invention

Another process of extracting glycosides from plants such as herbs using an aqueous two-phase system is provided. The process is presented in FIG. 2. The main difference between FIG. 2 and FIG. 1 is that the step 107 is replaced by the steps of 108, 109, and 110. Also, the final solid products obtained by the process of embodiment 2 contain higher concentration of glycosides than embodiment 1. In FIG. 2, the operations of steps 101–106 are the same as in the FIG. 1 described aforementioned, and the operations of steps 108–110 are described below.

After steps 105 and 106 are repeated adequately, all of the filtrates collected from step 106 are combined and sitting on the bench for about 12~18 hours, as shown in step 108, and the depositions are observed thereafter. Because the filtrates are rich in ethanol, the sitting temperature of the filtrates is chosen about –110° C. to 15° C. considering the melting point (m.p.) of ethanol (about –117.3° C.), and the preferred temperature is in the range of about –10° C. to 10° C.

Then, the depositions are removed by step of liquid-solid separation to obtain a final filtrate, as shown in step 109. The most general and simple method of liquid-solid separation is filtration, and it could be performed by means of the filter paper, filter aid, the organic membrane, or/and the sieve.

Finally, the final filtrate is concentrated in vacuo to give the final solid product rich in glyco sides, as shown in step 110.

According to the second embodiment of the invention, monosaccharide, disacchride and polysacchride, such as sennoside, geniposide, paeoniflorin, glycyrrhizin, quercitrin, puerarin, hesperidin, ginsenoside Rb1 and naringin, are extracted efficiently from herbs using the aqueous two-phase system.

The examples 4, 5, 6 and 7 illustrate the extraction of glycosides from dried gardenia fruit using an aqueous two-phase system according to the second embodiment of the invention.

EXAMPLE 4

Extracting glycosides from dried gardenia fruit using an aqueous two-phase system.

1. 200 g of dried gardenia fruit is mildly ground, mixed with 4000 g of water, and boiled for 30 minutes. After filtration, the filtrate is collected and the remaining gardenia fruit is mixed with fresh water, boiled, and filtered. The aqueous extractive solution is obtained by combining the two filtrates.
2. The extractive solution is concentrated to 625 g, and the solid content of the extractive solution concentrate is approximately 8.97% and this solid contains 27.82 wt % of geniposide as determined via HPLC.
3. 45 g (7.5%) of potassium dihydrogen phosphate ($KH_2PO_4$), 30 g (5%) of PE62 and 60 g (10%) of ethanol are added to 600 g of the extractive solution concentrate and then mixed thoroughly. The phase separation is performed by keeping the solution in a water bath at a temperature of 70° C. for 1–1.5 hour.
4. After phase separation, the lower layer is the aqueous while the upper layer is PE62. The aqueous layer is carefully removed and concentrated in vacuo to give a solid which is dried.
5. 300 ml of 95% ethanol is added to the dried solid, and the mixture is sonicated for 5 minutes.
6. Subsequently, the mixtures are centrifuged and the solid remaining is collected in a beaker. 300 ml of 95% ethanol is added to the residue (solids), followed by sonicating for 5 minutes.
7. The step 6 is repeated for several times, and all of the filtrates are combined and sitting on the bench for about 12~18 hours at a temperature of 4° C., and then the depositions in the filtrates are removed by the filter paper to obtain the final filtrate.
8. The final filtrate is concentrated in vacuo to give a final solid product which is dried and rich in glycosides. The weight of solid product is 12.62 g and the geniposide is 9.31 g determined by means of HPLC. The final solid product contains 73.77% by weight of geniposide. The total recovery yield of geniposide is 77%.

In this case, the purity of geniposide is increased from 27.82% to 73.77% using the aqueous two-phases system. The process does improve the purity of the glycosides.

EXAMPLE 5

In Example 5, the steps are performed the same as in example 4, except that the filter paper for filtrating the depositions in step 7 are replaced by the SABH calcined filter aid (made by GREFCO, inc., and composed of diatomite), to obtain a final solid product which is dried and rich in glycosides. The final solid product contains 80.97% by weight of geniposide. The total recovery yield of geniposide is 66%.

In this case, the purity of geniposide is increased from 27.82% to 80.97% using the aqueous two-phases system. The process does improve the purity of the glycosides.

EXAMPLE 6

In Example 6, the steps are performed the same as in example 4, except that the filter paper for filtrating the depositions in step 7 is replaced by the 0.22μ organic membrane (made by Micron separations inc., and composed of cellulose), to obtain a final solid product which is dried and rich in glycosides. The final solid product contains 71.9% by weight of geniposide. The total recovery yield of geniposide is 78%.

In this case, the purity of geniposide is increased from 27.82% to 71.9% using the aqueous two-phases system. The process does improve the purity of the glycosides.

EXAMPLE 7

In Example 7, the steps are performed the same as in example 4, except that the filter paper for filtrating the depositions in step 7 is replaced by the sieve of 400 mesh, to obtain a final solid product which is dried and rich in glycosides. The final solid product contains 76.5% by weight of geniposide. The total recovery yield of geniposide is 80%.

In this case, the purity of geniposide is increased from 27.82% to 76.5% using the aqueous two-phases system. The process does improve the purity of the glycosides.

According to the embodiments of the invention described above, the advantages of extracting glycosides using an aqueous two-phases system include:

1. The process is simplified due to simple procedures.
2. Extraction using aqueous two-phase system doesn't cause pollution as traditional method of extraction using organic solvent does. Part of the material also can be recycled and reused in the process.
3. With simple equipments and procedures, the final products with high concentration and high recycle rate of glycosides can be obtained, and the cost of production is also decreased by a wide margin.

While the invention has been described by way of examples and in terms of the preferred embodiments, it is to be understood that the invention is not limited to the disclosed embodiments. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A process of extracting glycosides from a plant, comprising the steps of:
   (a) grinding the plant and mixing with water to form an extractive solution;
   (b) adding about 5 wt %~30 wt % of salt and about 5 wt %~30 wt % of a polyol comprising a copolymer of ethylene oxide and propylene oxide, to the extractive solution and then mixing thoroughly to form an aqueous layer and a polyol layer of the copolymer of ethylene oxide and propylene oxide;
   (c) removing the aqueous layer and concentrating the aqueous layer to be a solid;
   (d) washing the solid with a solvent, and producing a filtrate and collecting the filtrate after filtration; and
   (e) concentrating the filtrate to obtain a final product rich in glycosides.

2. The process of extracting glycosides according to claim 1, wherein the plant is a herb.

3. The process of extracting glycosides according to claim 2, wherein the herb is selected from the group of a root of herbaceous peony, a dried gardenia fruit, and a rhubarb.

4. The process of extracting glycosides according to claim 1, wherein the glycosides include monosaccharide, disacchrides or polysacchride.

5. The process of extracting glycosides according to claim 4, wherein the glycoside consist of sennoside, geniposide, paeoniflorin, glycyrrhizin, quercitrin, puerarin, hesperidin, ginsenoside Rb1 and naringin.

6. The process of extracting glycosides according to claim 1, wherein step (a) further comprises steps of boiling and agitation.

7. The process of extracting glycosides according to claim 1, wherein step (a) further comprises the steps of adding water, boiling, and agitating for several times to form a crude extract for each time and each of the crude extract is collected and combined to form the extractive solution.

8. The process of extracting glycosides according to claim 1, wherein after step (a) and before step (b), a concentration procedure is further performed to concentrate the extractive solution to form an extractive solution concentrate with a solid content of about 1–10%.

9. The process of extracting glycosides according to claim 1, wherein the salt in step (b) is selected from the group consisting of dihydrogen phosphate, hydrogen phosphate and phosphate.

10. The process of extracting glycosides according to claim 1, wherein the salt in step (b) is selected from the group consisting of sulfate, chloride, oxalate, and acetate.

11. The process of extracting glycosides according to claim 1, wherein step (b) is performed at a temperature ranged from about 4° C. to 90° C.

12. The process of extracting glycosides according to claim 11, wherein step (b) is performed at the temperature ranged from about room temperature to 70° C.

13. The process of extracting glycosides according to claim 1, wherein step (b) is carried out in water bath.

14. The process of extracting glycosides according to claim 1, wherein an alcohol is further added to the extractive solution in step (b).

15. The process of extracting glycosides according to claim 14, wherein the alcohol is one of $C_1$–$C_4$ alcohols with a concentration ranged from about 0.01 wt %–30 wt %.

16. The process of extracting glycosides according to claim 15, wherein the alcohol is ethanol.

17. The process of extracting glycosides according to claim 1, wherein step (c) further comprises step of centrifugation in order to remove the aqueous layer.

18. The process of extracting glycosides according to claim 1, wherein the aqueous layer in step (c) and step (e) is concentrated in vacuo.

19. The process of extracting glycosides according to claim 1, wherein the concentration of the solvent in step (d) used to wash the solid is approximately 60%–99%.

20. The process of extracting glycosides according to claim 19, wherein the solvent is alcohol.

21. The process of extracting glycosides according to claim 20, wherein the solvent is one of $C_1$–$C_4$ alcohols.

22. The process of extracting glycosides according to claim 21, wherein the solvent is ethanol.

23. The process of extracting glycosides according to claim 1, wherein after the solid is washed, step (d) further comprises steps of
   (d1) sonicating; and
   (d2) centrifugating to separate a first filtrate and a first residue;
   wherein in step (e) the first filtrate is concentrated to obtain the final product rich in glycosides.

24. The process of extracting glycosides according to claim 23, wherein steps are further performed after step (d2), comprising:
   (d3) sonicating; and
   (d4) centrifugating to separate the solid and liquid, and forming a second filtrate and a second residue;
   wherein in the step (e) the first filtrate and the second filtrate are concentrated to obtain the final product rich in glycosides.

25. The process of extracting glycosides according to claim 1, wherein the filtrate is further set stilly at a temperature of −110° C.~15° C. to separate a deposition from liquid after step (d), and then the liquid is collected as a final filtrate and concentrated to obtain the final product rich in glycosides.

26. The process of extracting glycosides according to claim 25, wherein the filtrate is set preferably at a temperature of about −10° C.~10° C. for about 12–18 hours.

27. The process of extracting glycosides according to claim 25, wherein means for separating the deposition from the liquid is selected from the group consisting of a filter paper, a filter aid, an organic membrane, and a sieve.

28. The process of extracting glycosides according to claim 1, wherein a non-toxic organic solvent is used to wash the solid in step (d).

29. The process of extracting glycosides according to claim 28, wherein the non-toxic organic solvent is ethanol.

30. The process of extracting glycosides according to claim 1, wherein the polyol comprises PE62.

31. An aqueous two-phases system for extracting glycosides from a plant, comprising:

an extractive solution;

about 5 wt %~30 wt % of salt; and about 5 wt %~30 wt % of a polyol comprising a copolymer of ethylene oxide and propylene oxide, wherein the weight percentage of the salt and the polyol are calculated based on the weight of the extractive solution.

32. The aqueous two-phases system according to claim 31, wherein the system further comprises alcohol with a concentration of 0.01 wt %–30 wt %, approximately.

33. The aqueous two-phases system according to claim 32, wherein the alcohol is one of $C_1$–$C_4$ alcohols.

34. The aqueous two-phases system according to claim 33, wherein the alcohol is ethanol.

35. The aqueous two-phases system according to claim 31, wherein the salt is selected from the group consisting of dihydrogen phosphate, hydrogen phosphate and phosphate.

36. The aqueous two-phases system according to claim 31, wherein the salt is selected from the group consisting of sulfate, chloride, oxalate, and acetate.

37. The aqueous two-phases system according to claim 31, wherein the polyol comprises PE62.

* * * * *

UNITED STATES PATENT AND TRADEMARK OFFICE
CERTIFICATE OF CORRECTION

| | | |
|---|---|---|
| PATENT NO. | : 6,635,758 B2 | Page 1 of 1 |
| APPLICATION NO. | : 10/042311 | |
| DATED | : October 21, 2003 | |
| INVENTOR(S) | : I-Hong Pan et al. | |

It is certified that error appears in the above-identified patent and that said Letters Patent is hereby corrected as shown below:

On the Title Page, Item 75 (Inventors)

Please change the listing of Inventors to read as follows:

-- I-Hong Pan, Hsinchu (TW);
  Chu-Hsun Lu, Kaohsiung (TW);
  Hsi-Ho Chiu, Hsinchu (TW);
  Lain-Tze Lee, Hsinchu (TW);
  Huei-Ju Liu, Nantou (TW);
  Hsin-Jan Yao, Yunlin (TW) --

Signed and Sealed this

Twenty-sixth Day of January, 2010

David J. Kappos
*Director of the United States Patent and Trademark Office*